(12) United States Patent
Rado (10) Patent No.: US 10,327,470 B2
(45) Date of Patent: Jun. 25, 2019

(54) APPARATUS AND METHODS FOR VAPORIZING ESSENTIAL OILS AND WAXES

(71) Applicant: Lubby Holdings, LLC, Torrance, CA (US)

(72) Inventor: J. Christian Rado, Torrance, CA (US)

(73) Assignee: Lubby Holdings, LLC, Torrance, CA (US)

( * ) Notice: Subject to any disclaimer, the term of this patent is extended or adjusted under 35 U.S.C. 154(b) by 0 days.

(21) Appl. No.: 15/991,817

(22) Filed: May 29, 2018

(65) Prior Publication Data

US 2018/0271147 A1 Sep. 27, 2018

Related U.S. Application Data

(63) Continuation of application No. 14/658,091, filed on Mar. 13, 2015, now Pat. No. 10,021,909.

(60) Provisional application No. 61/952,602, filed on Mar. 13, 2014.

(51) Int. Cl.

| *A24F 47/00* | (2006.01) |
|---|---|
| *A24F 1/30* | (2006.01) |
| *A61M 15/06* | (2006.01) |
| *A61M 11/04* | (2006.01) |
| *A61L 9/03* | (2006.01) |
| *A61M 16/16* | (2006.01) |

(52) U.S. Cl.
CPC .............. *A24F 47/00* (2013.01); *A24F 1/30* (2013.01); *A61M 11/048* (2014.02); *A61M 15/06* (2013.01); *A61L 9/03* (2013.01); *A61M 16/16* (2013.01)

(58) Field of Classification Search
CPC .......... A24F 47/00; A24F 47/008; A24F 1/30; A61L 2/00; A61L 9/00; A61L 9/103; H05B 1/0244; H05B 1/02

USPC ........ 219/494, 497, 505; 131/273, 194, 335, 131/336; 392/386, 387, 390, 394, 404
See application file for complete search history.

(56) References Cited

U.S. PATENT DOCUMENTS

| 2,104,266 A | 1/1938 | McCormick |
| 3,200,819 A | 8/1965 | Gilbert |
| 4,947,874 A | 8/1990 | Brooks et al. |
| 7,832,410 B2 | 11/2010 | Hon |

(Continued)

OTHER PUBLICATIONS

Office Action from USPTO dated Sep. 12, 2017 for related U.S. Appl. No. 14/658,091.

(Continued)

*Primary Examiner* — Mark H Paschall
(74) *Attorney, Agent, or Firm* — Klein, O'Neill & Singh, LLP (57) ABSTRACT

A vaporizer assembly is shaped and configured to fit partially into a downstem of a water pipe. The vaporizer assembly includes a housing including an upper portion and a lower portion. The lower portion has a smaller diameter, and fits in the downstem. The upper portion of the vaporizer assembly includes a bowl or dish, and a heat source is enclosed within the housing and positioned and configured to selectively heat the bowl or dish. A body of the vaporizer adjacent the bowl includes vapor passages. One or more passages are also formed in the lower portion. Thus, essential oils or waxes placed in the bowl can be vaporized by the heat. The generated vapor may flow from the bowl into and through the vapor passages and lower portion passage and into the waterpipe's downstem.

20 Claims, 7 Drawing Sheets

(56) References Cited

U.S. PATENT DOCUMENTS

| | | |
|---|---|---|
| 8,156,944 B2 | 4/2012 | Han |
| 8,365,742 B2 | 2/2013 | Hon |
| 8,375,957 B2 | 2/2013 | Hon |
| 8,393,331 B2 | 3/2013 | Hon |
| 8,794,231 B2 | 8/2014 | Thorens et al. |
| 8,915,254 B2 | 12/2014 | Monsees et al. |
| 9,220,303 B2 | 12/2015 | Li et al. |
| 9,380,811 B2 | 7/2016 | Chung |
| 2013/0152922 A1 | 6/2013 | Benassayag et al. |
| 2013/0247910 A1 | 9/2013 | Postma |
| 2013/0298905 A1 | 11/2013 | Levin et al. |
| 2014/0041655 A1 | 2/2014 | Barron et al. |
| 2015/0282524 A1 | 10/2015 | Elhalwani |
| 2016/0029696 A1 | 2/2016 | Obeidallah |

OTHER PUBLICATIONS

Notice of Allowance from USPTO dated May 10, 2018 for related U.S. Appl. No. 14/658,091.

APPARATUS AND METHODS FOR VAPORIZING ESSENTIAL OILS AND WAXES

CROSS-REFERENCE TO RELATED APPLICATIONS

The application is a continuation application of U.S. application Ser. No. 14/658,091, which was filed on Mar. 13, 2015; which is based on and claims the benefit of U.S. Provisional Application No. 61/952,602, which was filed on Mar. 13, 2014, the entireties of which are hereby incorporated by references.

BACKGROUND

The present disclosure relates to the field of apparatus and methods for vaporizing essential oils and waxes A vaporizer is a device used to vaporize the active ingredients of plant material for the purpose of inhalation. Vaporization is an alternative to burning (smoking) that avoids the inhalation of many irritating toxic and carcinogenic by-products. In some forms, the plant material that is vaporized is an extract in the form of an oil or a wax. In some vaporization processes, the oil or wax is vaporized in a water pipe. The user uses a handheld blowtorch to heat a metal surface until the metal surface reaches a desired temperature, which may be indicated by a glowing orange hue. The user then places a drop of oil or wax on the hot surface with an implement, such as a glass rod or a dental pick. The oil or wax then melts, boils, and vaporizes. The user then inhales through the water pipe to draw the vapor into the user's lungs. This process is not only cumbersome, but also potentially dangerous, since it involves use of a handheld blowtorch and an exposed, glowing hot titanium surface.

SUMMARY

There is a need in the art for a simpler and safer alternative for vaporizing essential oils and waxes.

In accordance with one embodiment, the present specification describes a vaporizing apparatus, comprising a tubular housing, a heating surface, a heat source and a vapor path. The tubular housing has an upper end and a lower end. The heating surface is arranged adjacent the upper end of the housing. The heat source is disposed adjacent the heating surface. The vapor path is defined within the housing between the heating surface and a lower opening at the lower end of the housing. The vaporizing apparatus is configured so that a combustible material on the heating surface generates a vapor when the heat source is activated, and such vapor follows the vapor path to exit the vaporizing apparatus through the lower opening.

In some such embodiments, a tapered part of the housing has a tapered outer diameter that decreases moving toward the lower end of the housing.

In additional embodiments, an upper portion of the housing has an outer diameter greater than an outer diameter of a lower portion of the housing, and the tapered part is in the lower portion of the housing.

Some embodiments are configured for use in connection with a water pipe having a downstem with a downstem inner diameter. In some such embodiments, a first portion of the tapered part has a diameter less than the downstem inner diameter and a second portion of the tapered part has a diameter greater than or equal to the downstem inner diameter. The tapered part engages an inner surface of the downstem and some of the tapered part extends into the downstem.

In further embodiments, a body is mounted within the housing and defines a bowl, and wherein the bowl comprises the heating surface.

Some such embodiments additionally comprise a plurality of passages formed along the length of the body within the housing, and the vapor path extends through at least one of the plurality of passages.

In some embodiments, the heat source comprises a flame-based heater, and a flame chamber is defined within the body and opposite the heating surface.

In yet additional embodiments the heat source comprises an electricity-powered heating element.

Some such embodiments additionally comprise a controller and an actuator button, the controller configured to control power delivery to the heating element in connection with a plurality of control modes.

In further embodiments, the controller is configured so that a user can select between the plurality of control modes by actuating the actuator button according to a preset pattern.

In yet further embodiments, the controller is configured to prevent energizing of the heating element beyond an elapsed time.

In still further embodiments, in a first mode the controller is configured to energize the heating elements for a specified time period when the actuator button is actuated.

Some embodiments additionally comprise a battery assembly that extends through and out of the lower end of the housing when the battery assembly is engaged and electrically connected to the vaporizing apparatus.

Yet additional embodiments additionally comprise a lid (carb cap) configured to be removably attached to the upper end of the housing so as to define a vaporizing chamber between the lid and the heating surface when the lid is attached.

In accordance with yet another embodiment, the present disclosure provides a method of using a vaporizing apparatus. The method includes placing a combustible material on a heating surface defined in a cavity formed in a body placed in a tubular housing of the vaporizing apparatus. The method further includes placing the vaporizing apparatus into a downstem of a water pipe so that a portion of the tubular housing of the vaporizing apparatus extends into the downstem and a portion of the tubular housing engages an inner surface of the downstem, and actuating a heat source so that at least a portion of the combustible material is vaporized into a vapor. The vapor is drawn along a vapor path from the heating surface, through the tubular housing and into the downstem, and further through the water pipe.

Some such amendments can additionally comprise selecting between a plurality of modes of operation of the heating element.

DESCRIPTION

The present specification describes embodiments with reference to the drawings. In the drawings, reference numbers label elements of the present embodiments. These reference numbers are reproduced below in connection with the discussion of the corresponding drawing features.

The embodiments of the present apparatus and methods for vaporizing essential oils and waxes are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

Figure 1:
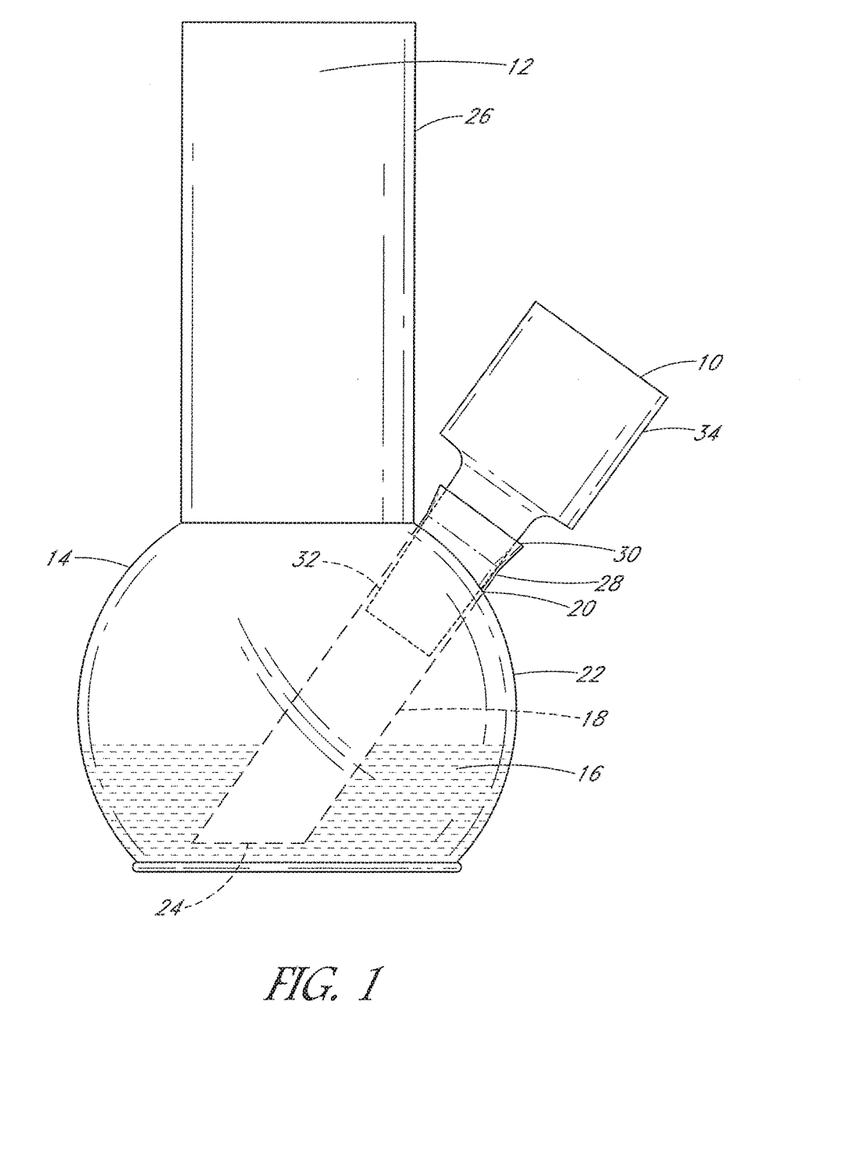
FIG. 1 is a schematic side elevation view of one of the present embodiments of a vaporizing apparatus in combination with a typical water pipe.

With initial reference to FIG. 1, an embodiment of a vaporizing apparatus 10 is disclosed in conjunction with a typical water pipe 12, which is also commonly referred to as a bong. The water pipe 12 includes a reservoir 14 for holding water 16, a tubular downstem 18 extending through an opening 20 in the sidewall 22 of the reservoir 14, and a tubular stem 26 extending upward from the reservoir 14. A lower opening 24 of the downstem 18 is disposed below the waterline so that the lower opening 24 is submerged in the water 16. An upper end 28 of the downstem is arranged outside the reservoir 14, and preferably includes an upper opening 30 which, in the illustrated embodiment, is flared.

During use, vapor from the vaporizing apparatus 10 is drawn through the flared upper opening 30 through the lower opening 24 and into the water 16, from which it is further drawn through the stem 26 before being inhaled by the user. The water 16 in the reservoir 14 filters and cools the vapor from the vaporizing apparatus 10 prior to the vapor passing into the user's lungs, as described in further detail below. The reservoir 14 is typically filled only partially with water 16, with sufficient water 16 being added to submerge the lower opening 24 of the downstem 18 but with a substantial volume of air filling the remainder of the reservoir 14 above the waterline.

With continued reference to FIG. 1, the illustrated vaporizing apparatus comprises a lower portion 32 and an upper portion 34. As shown, the upper portion 34 has a greater diameter than the lower portion 32. More specifically, the lower portion 32 is sized so that at least a portion of the lower portion 32 fits through the upper opening 30 of the downstem 18, and extends into the downstem 18, while the upper portion 34 has a diameter greater than that of the downstem 18. While in some embodiments the diameter of the lower portion may be constant, in the illustrated embodiment, a portion of the lower portion 32 is tapered so that part of the lower portion 32 fits into the downstem 18, and another part of the lower portion 32 engages the upper end 28 of the downstem.

A typical downstem 18 has a length within the range of about 2" to about 6", and an inner diameter within the range of about 10 mm to about 20 mm, with variations outside these ranges for manufacturing tolerances, and with shorter, longer, narrower, and wider downstems also being available. Thus, in some embodiments the lower portion 32 of the vaporizing apparatus 10 may have a length within the range of about 2" to about 5", and an outer diameter within the range of about 9.5 mm to about 19.5 mm, with variations outside these ranges for manufacturing tolerances. The vaporizing apparatus 10 is thus configured to be compatible with off-the-shelf water pipes that are manufactured according to industry standards. However, it should be understood that the present embodiments are not limited by any of the dimensions specified herein.

Figure 2:
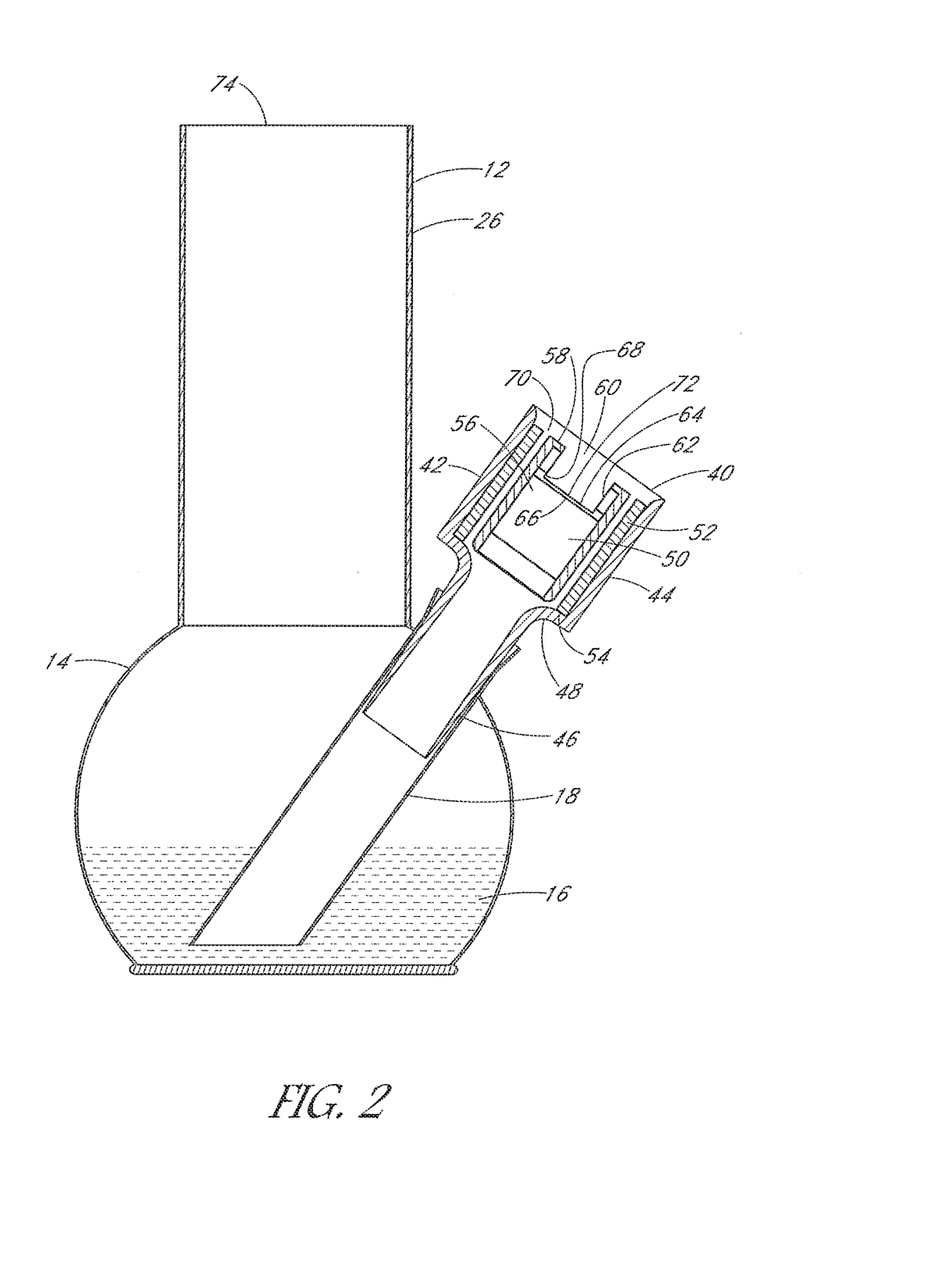
FIG. 2 is a partial cross-sectional side elevation view of one of the present embodiments of a vaporizing apparatus in combination with a typical water pipe.

FIG. 2 illustrates another embodiment of a vaporizing apparatus 40 in combination with a typical water pipe 12. The vaporizing apparatus 40 includes a housing 42 that is generally tubular and includes an upper portion 44 and a lower portion 46. The upper portion 44 defines a first, larger diameter, and the lower portion 46 defines a second, smaller diameter. The upper and lower portions 44, 46 converge in a flared region 48 of the housing 42. The exterior surface of the lower portion 46 may include a taper angle so that the housing 42 is snugly received within the downstem 18. For example, the exterior taper angle may be within the range of about 4° to about 6°, with variations outside this range for manufacturing tolerances.

The upper portion 44 of the housing 42 defines an interior chamber 50 that receives a body portion 52. At its lower end, the body portion 52 seats against an interior shoulder 54 of the housing 42 that is located at the junction of the upper housing portion 44 and the lower housing portion 46. The body 52 may be secured within the interior chamber 50 of the housing 42 by any desired means, such as, without limitation, threads and/or magnets (not shown). The illustrated body portion 52 is generally cylindrical and defines an interior space 56 that is open at either end. The upper end of the body 52 includes in inwardly extending flange 58 defining an upper opening 60.

In the illustrated embodiment, an annular spacer 62 seats beneath the flange 58, and a heating surface 64 seats beneath the spacer 62. The heating surface 64, which may also be referred to as a tray, dish or bowl, includes a flat, disk-shaped interior plate 66 and a rim portion 68 circumscribing the plate 66. The rim portion 68 has a greater thickness than the plate 66, and together the plate 66 and the rim 68 form a shallow flat-bottomed bowl for receiving combustible material, such as essential oils and/or waxes, as described in further detail below. The heating surface 64 is advantageously recessed within the vaporizing apparatus 40, located beneath the flange 58 and the spacer 62. During use, the heating surface 64 gets hot enough to vaporize combustible material placed thereon. Thus, the recessed location for the heating surface 64 reduces the likelihood that a user will suffer a burn from inadvertently touching the hot heating surface 64.

With continued reference to FIG. 2, a sidewall of the body 52 includes at least one longitudinally extending passage 70, and in some embodiments may include a plurality of radially spaced longitudinal passages 70. The passages 70, which are open at either end, provide flow paths for vapor produced adjacent the heating surface 64, as described below. In alternative embodiments, the longitudinal passages 70 may be omitted, and one or more longitudinally extending flutes or grooves (not shown) may be provided along the outer surface of the body 52, such as a plurality of radially spaced longitudinal flutes or grooves.

The embodiment illustrated in FIG. 2 further includes a heat source (not shown). The heat source may comprise any device or apparatus capable of producing heat, such as a flame producing device, a resistive heating coil, etc. The heat source may be located at least partially within the body 52, such as beneath the heating surface 64. When activated, the heat source generates heat that is transferred to the heating surface 64. Combustible material, such as essential oils and/or waxes, located on the upper surface of the heating surface 64 are heated through conduction from the heating surface 64. The essential oils and/or waxes are vaporized, and the vapor is drawn through the vaporizing apparatus 40 and into the user's lungs, as described below.

During use, the user places combustible material, such as essential oils and/or waxes, on the upper surface 72 of the heating surface 64. The user then activates the heat source to heat the heating surface 64, thereby vaporizing at least a portion of the combustible material. (In alternative embodiments, according to user preference, the user may activate the heat source to heat the heating surface 64 prior to placing the combustible material on the heating surface 64.) The user places his or her mouth on the upper rim 74 of the water pipe's stem 26 with sufficient force to create a substantially airtight seal around the rim 74. The user then inhales, creating suction that draws air inward through the vaporizing apparatus 40. The air, along with the vapor produced at the heating surface 64, flows along a flow path from the heating surface 64 through the passages 70 in the body 52, downward through the downstem 18, through the water 16 in the reservoir 14, upward through the stem 26, and ultimately into the user's mouth and lungs.

Figure 3:
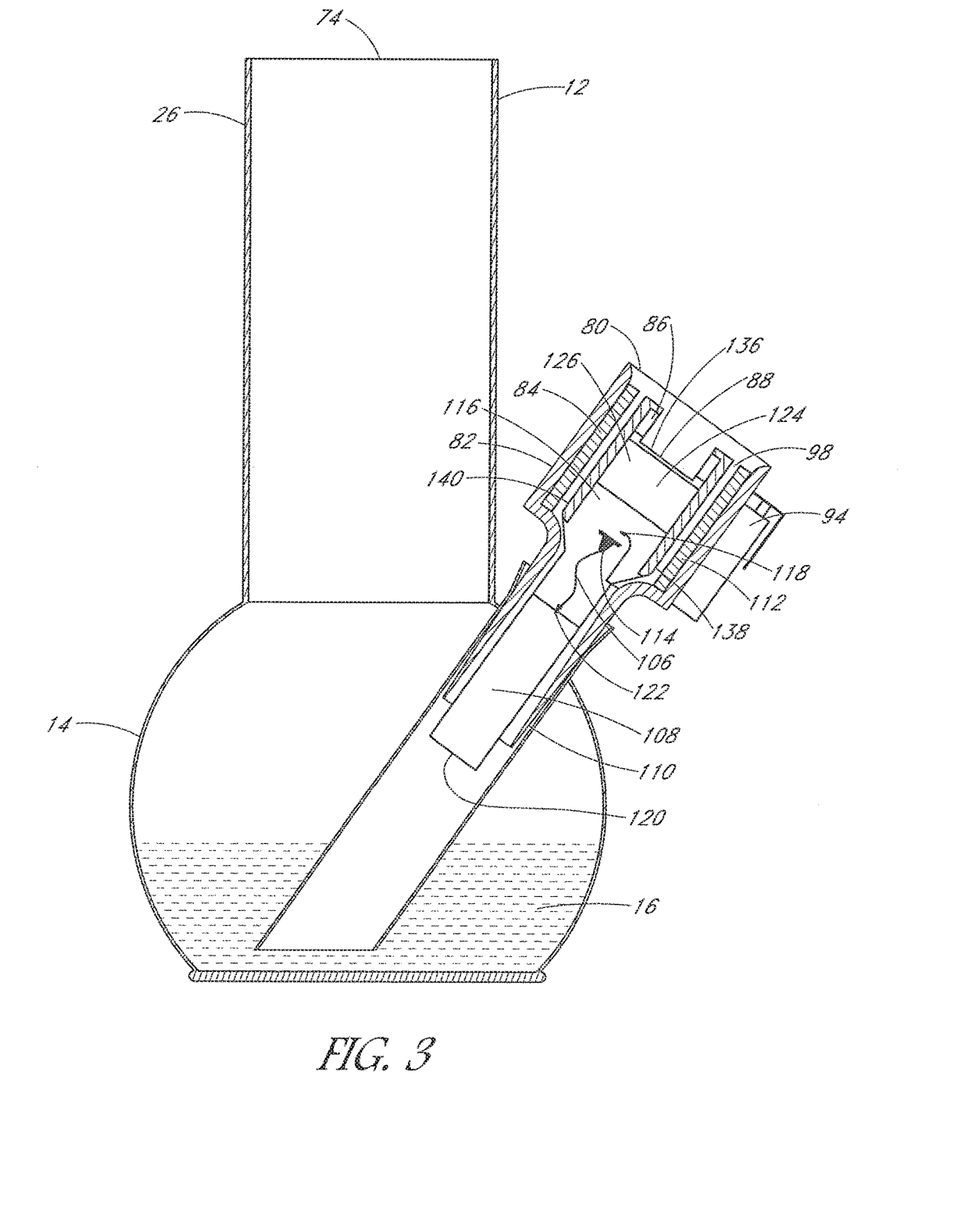
FIG. 3 is a partial cross-sectional side elevation view of another of the present embodiments of a vaporizing apparatus in combination with a typical water pipe.
Figure 4:
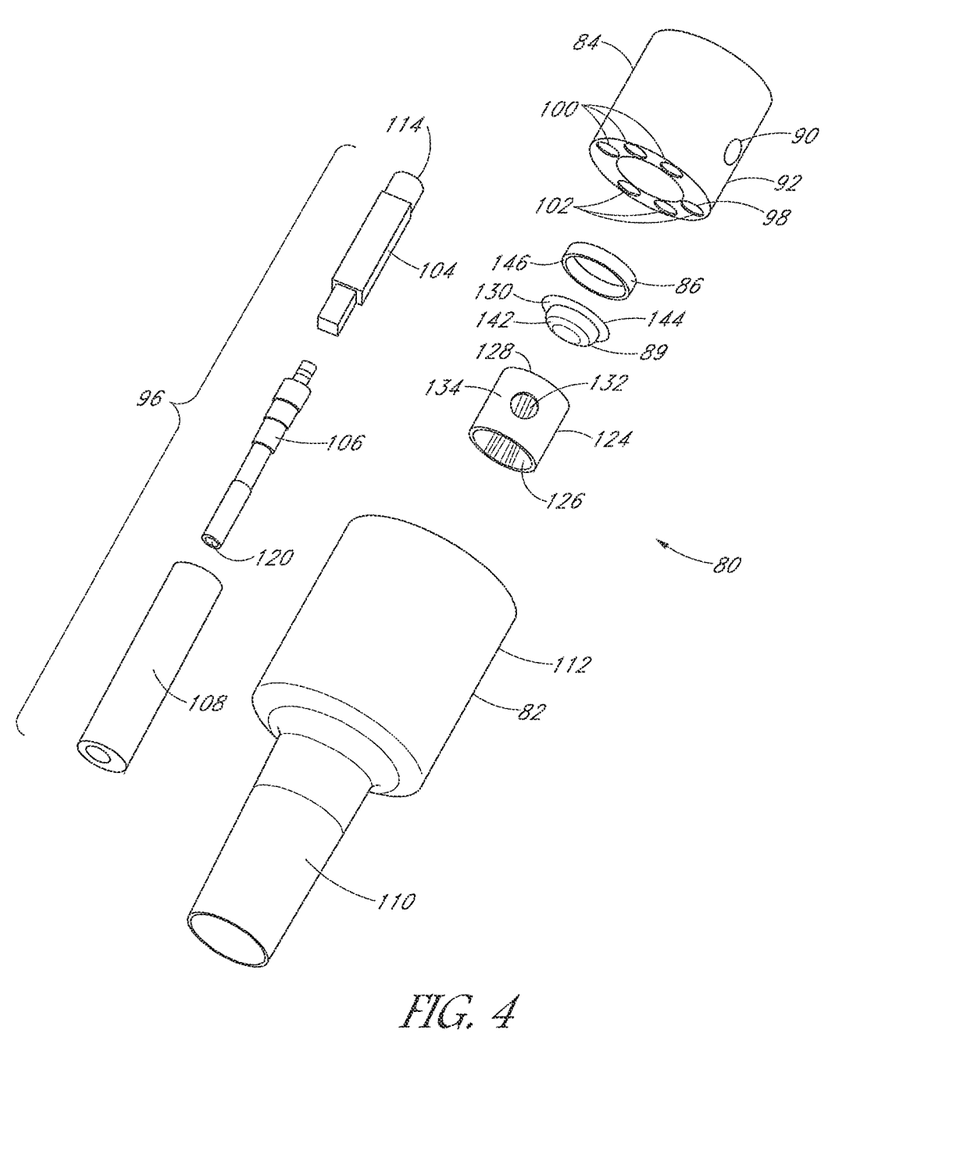
FIG. 4 is an exploded side perspective view of the vaporizing apparatus of FIG. 3.

FIG. 3 is a partial cross-sectional side elevation view of another embodiment of a vaporizing apparatus 80 in combination with a typical water pipe 12. FIG. 4 is an exploded side perspective view of the vaporizing apparatus 80 of FIG. 3. Similar to the embodiment of FIG. 2, the vaporizing apparatus 80 includes a housing 82 that receives a body 84, a spacer 86, and a heating surface 88/89. These components share many of the structural features described above with respect to their counterparts in the embodiment of FIG. 2. Therefore, features that these embodiments have in common will not be repeated here, but are nevertheless clearly depicted in FIGS. 3 and 4 and are part of these embodiments.

With reference to FIG. 4, the body 84 includes a radially extending through hole 90 in the sidewall 92. While not visible in FIG. 4, the through hole 90 may continue through the opposite side of the body 84. With additional reference to FIG. 3, the through hole 90 accommodates an ignition button 94 that activates a flame producing device. In the illustrated embodiment, the flame producing device comprises a torch-type piezoelectric lighter 96, which is described in further detail below. The illustrated body 84 includes a plurality of radially spaced longitudinal passages 98. In the illustrated embodiment, six passages 98 are provided with a first group 100 of three passages 98 positioned toward a first side of the body 84 and a second group 102 of three passages 98 positioned toward a second side of the body 84. The through hole 90 preferably is positioned along a portion of the body 84 sidewall that is between the first and second groups 100, 102 of passages 98 such that the through hole 90 is not in fluid communication with any of the passages 98 or the vapor flowing therethrough.

With continued reference to FIGS. 3 and 4, in the illustrated embodiment, the piezoelectric lighter 96 comprises a piezoelectric igniter 104 coupled to a fuel line 106 and a fuel reservoir 108. The components of the piezoelectric lighter 96 preferably are contained at least partially within the housing 82. With particular reference to FIG. 3, the fuel reservoir 108 and the fuel line 106 are received within the lower portion 110 and part of the upper portion 112 of the housing 82, with a discharge port/nozzle 114 of the fuel line 106 extending into the upper portion 112 of the housing 82 and into the space 116 defined within the body 84. The lead 118 of the piezoelectric igniter 104 is positioned adjacent the discharge port 114 of the fuel line 106 to facilitate igniting the fuel from the fuel reservoir 108 as it is expelled through the discharge port 114. A lower end of the fuel line 106 includes a fill nozzle 120 for adding additional fuel, such as butane, to the fuel reservoir 108 from a fuel source (not shown). An upper end of the fuel reservoir 108 includes a release valve 122 that feeds fuel into the fuel line 106 and into the discharge port 114.

While the illustrated flame producing device comprises a torch-type lighter with a piezoelectric igniter 104, the illustrated flame producing device is only one example and is not limiting. For example, and without limitation, in alternative embodiments the flame producing device may comprise a non-torch-type butane lighter.

With continued reference to FIG. 4, the vaporizing apparatus 80 further comprises a flame chamber 124 formed in the body 84. In the illustrated embodiment, the flame chamber 124 is generally cylindrical and defines an interior space 126. The outside diameter of the flame chamber 124 preferably is closely matched to the inside diameter of the body 84, such that the flame chamber 124 is snugly received within the interior 116 of the body 84, with an upper end 128 (FIG. 4) of the flame chamber 124 bearing against a lower surface 130 of the heating surface 88/89. As best shown in FIG. 4, the flame chamber 124 includes a radially extending through hole 132 in its sidewall 134. The through hole 132 preferably aligns with the through hole 90 in the body 84 to accommodate the button 94 of the piezoelectric lighter 96. As shown in FIG. 3, the flame chamber 124 is located adjacent the discharge port 114 of the fuel line 106. The flame produced by the piezoelectric lighter 96 is thus located within the flame chamber 124 and just beneath the heating surface 88/89. When the piezoelectric lighter 96 is ignited, the flame heats the heating surface 88/89 to vaporize combustible material located on the upper surface 136 of the heating surface 88/89, as described in further detail below.

In the illustrated embodiment, an upper end of the fuel reservoir 108 includes threads 138 (FIG. 3), and a lower end of the body 84 includes threads 140. The fuel reservoir 108 is thus removably threadingly coupled to the body 84 by engagement of the mating threads 138, 140. The fuel reservoir 108 may bear against a lower end of the flame chamber 124 to positively locate the spacer 86, the heating surface 88/89, and the flame chamber 124 within the body 84. While not shown, another annular spacer may be located between the upper end of the fuel reservoir 108 and the lower end of the flame chamber 124.

FIGS. 3 and 4 illustrate alternative configurations for the heating surface 88/89. For example, in FIG. 3, the heating surface 88 is similar to that described above and shown in FIG. 2. In FIG. 4, the heating surface 89 includes a convex/concave central portion 142 and an upper rim portion 144. The rim 144 is shaped as a flat annulus and extends radially outward from the upper edge of the central portion 142. The rim 144 is received between the upper end 128 of the flame chamber 124 and the lower surface 146 of the spacer 86 such that the central portion 142 of the heating surface 89 extends downward into the upper end 128 of the flame chamber 124.

Figure 5:
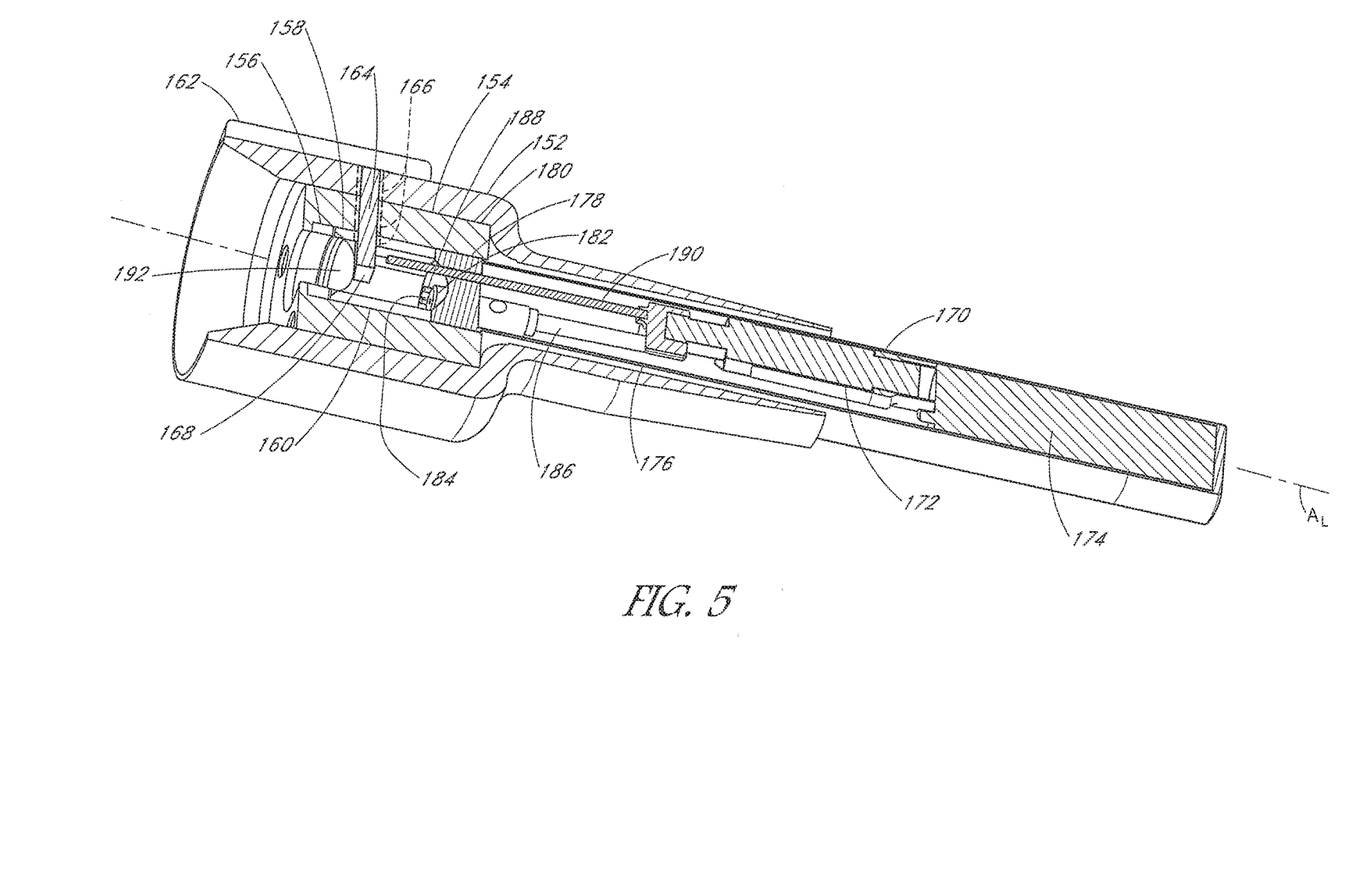
FIG. 5 is a cross-sectional side perspective view of another of the present embodiments of a vaporizing apparatus.

With next reference to FIG. 5, which is a cross-sectional side perspective view of another embodiment of a vaporizing apparatus 150. Similar to the embodiments described above, the vaporizing apparatus 150 includes a housing 152 that receives a body 154. The body 154 receives a spacer 156, a heating surface 158, and a flame chamber 160. These components share many of the structural features described above with respect to their counterparts in the embodiment described above. Therefore, features that these embodiments have in common will not be repeated here, but are nevertheless clearly depicted in FIG. 5 and are part of these embodiments.

An ignition button 162 is received on the exterior of the housing 152. In the illustrated embodiment, the ignition button 162 is slidable along the housing 152 in a direction parallel to a longitudinal axis $A_L$ of the vaporizing apparatus 150. A biasing member (not shown) biases the ignition button 162 toward the upper end of the housing 152, such that when the ignition button 162 is slid downward along the housing 152 and released it returns to the at rest position shown in FIG. 5.

The ignition button 162 includes a radial extension 164 that extends radially inward through openings 166 in the housing 152, the body 154, and the flame chamber 160. An inward end 168 of the radial extension 164 protrudes into the interior space of the flame chamber 160, as shown in FIG. 5. The radial extension 164 transmits motion of the ignition button 162 to a piezoelectric lighter 170 to activate the vaporizing apparatus 150, as described below.

The piezoelectric lighter 170 includes a piezoelectric igniter 172, a fuel reservoir 174, and a casing 176. The casing 176 is generally cylindrical, and includes an interior space that accommodates the fuel reservoir 174 and the piezoelectric igniter 172. An upper end 178 of the casing 176 engages the lower end 180 of the body 154 to secure the casing 176 to the body 154, which is in turn secured to the housing 152. The casing 176 and the body 154 may engage one another with threads (not shown) or by any other suitable means of securing the casing 176 to the body 154, such as a press fit.

The piezoelectric lighter 170 further includes a discharge port/nozzle 182. An outlet end of the discharge port 182 is located within the flame chamber 160. A fuel line 186 extends between the fuel reservoir 174 and the discharge port 182. When the piezoelectric lighter 170 is activated, fuel is carried from the fuel reservoir 174 through the fuel line 186 and to the discharge port 182 where it is expelled and burned. A lead 188 of the piezoelectric igniter 172 is positioned adjacent the discharge port 182 to facilitate igniting the fuel as it is expelled through the discharge port 182.

The piezoelectric lighter 170 further includes a rod 190 that extends between the inward end 168 of the ignition button radial extension 164 and the piezoelectric igniter 172. The rod 190 is translatable within the casing 176 in a direction parallel to the longitudinal axis $A_L$ of the vaporizing apparatus 150. When the user slides the ignition button 162 downward along the exterior of the housing 152, the radial extension 164 also moves downward, forcing the rod 190 downward. Motion of the rod 190 toward the piezoelectric igniter 172 activates the igniter 172, producing a spark at the lead 188 within the flame chamber 160 and activating the flow of fuel from the reservoir 174 through the fuel line 186 and out the discharge port 182. The spark ignites the fuel, producing a flame within the flame chamber 160 that heats the heating surface 158 to vaporize combustible material located on the upper surface 192 of the heating surface 158, as described in further detail below.

During use, the user places combustible material, such as essential oils and/or waxes, on the upper surface 136, 192 of the heating surface 88/89, 158. The user then depresses the ignition button 94, 162 of the piezoelectric lighter 96, 170, which produces a flame inside the flame chamber 124, 160. The flame causes the heating surface 88/89, 158 to get hot, thereby vaporizing at least a portion of the combustible material. (In alternative embodiments, according to user preference, the user may depress the ignition button 94, 162 to cause the heating surface 88/89, 158 to get hot prior to placing the combustible material on the heating surface 88/89, 158.) With reference again to FIG. 3, in use, the user places his or her mouth against the upper rim 74 of the water pipe's stem 26 with sufficient force to create a substantially airtight seal around the rim 74. The user then inhales, creating suction that draws air inward through the vaporizing apparatus 80, 150. The air, along with the vapor produced at the heating surface 88/89, 158, flows through the passages 98 in the body 84, downward through the downstem 18, through the water 16 in the reservoir 14, upward through the stem 26, and ultimately into the user's mouth and lungs.

In the embodiments discussed herein that employ a flame to heat the heating surface, the flame produced by the integrated piezoelectric lighter is advantageously contained within the flame chamber, and heat produced by the flame is transferred to the combustible material via conduction through the heating surface of the bowl. Thus, the flame is never exposed outside of the housing.

In additional embodiments, other methods and apparatus can be employed to heat the heating surface so as to vaporize the combustible material. For example, with reference next to FIGS. 6 and 7, another embodiment of a vaporizing apparatus 200 is depicted, which vaporizing apparatus employs electric power to vaporize the combustible material.

Figure 6:
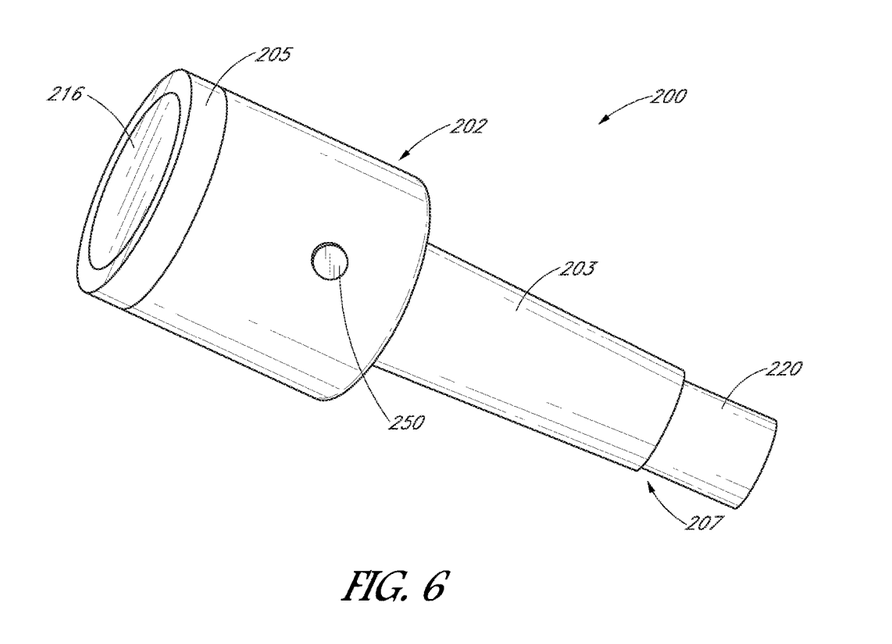
FIG. 6 is a perspective view of another embodiment of a vaporizing apparatus.
Figure 7:
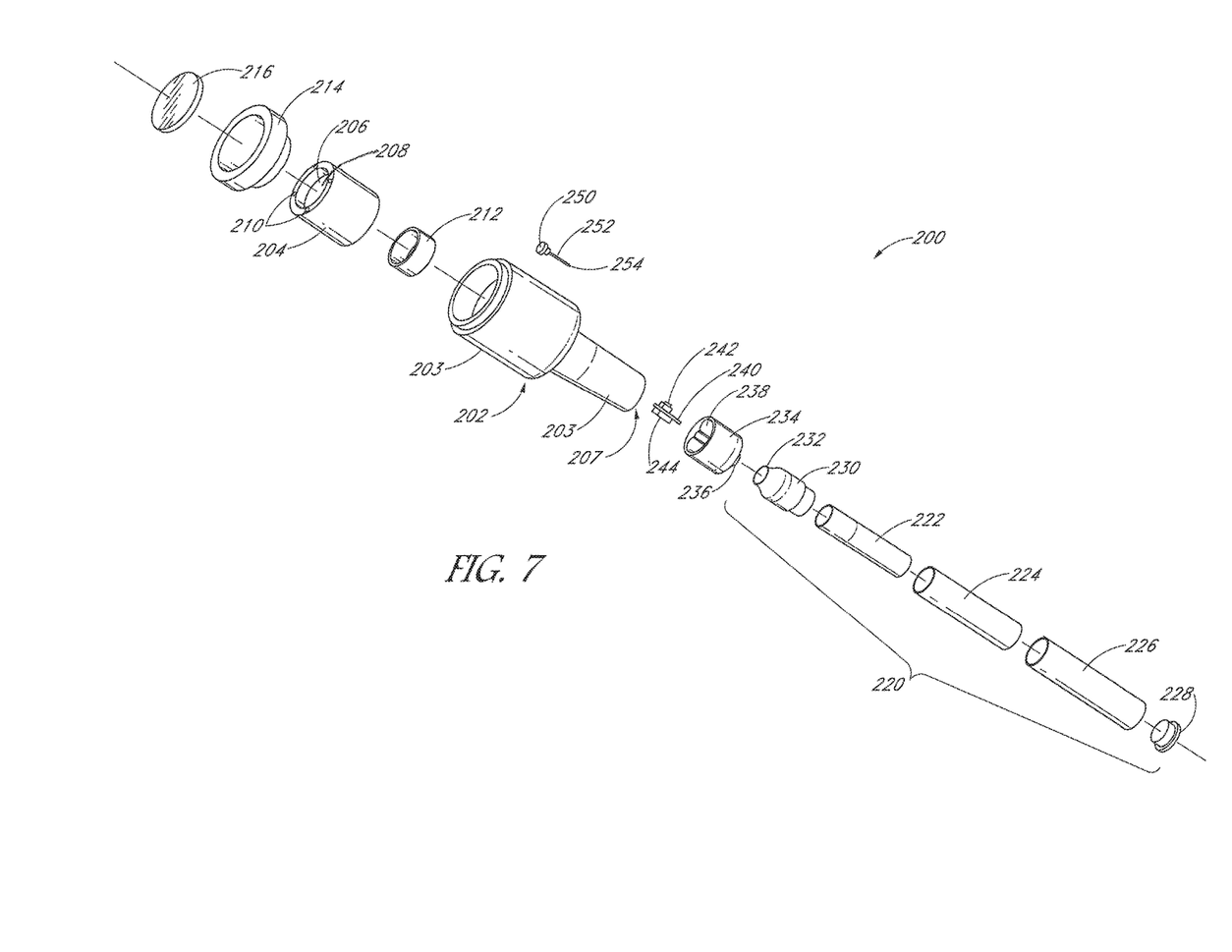
FIG. 7 is an exploded view of the embodiment of FIG. 6.

The illustrated vaporizer 200 comprises a housing 202 which, as in other embodiments, has a lower portion 203 and an upper portion 205. A diameter of the upper portion 205 is greater than a diameter of the lower portion 203, and a shoulder separates the upper and lower portions. Part of the lower portion 203 has a constant diameter, and another part of the lower portion 203 tapers moving toward a lower opening 207.

A body 204, which can also be referred to as a slug, is arranged within the upper portion 203 of the housing 202. The illustrated body 204 includes a cavity defining a bowl 206 that defines a heating surface 208. The bowl 206 is configured to receive and contain combustible material such as essential oils and waxes. As discussed above, when the heating surface 208 is heated, the combustible material will vaporize. As in other embodiments, longitudinally-extending passages 210 can be formed in the body 204 so as to provide a path for vapor generated at the bowl 206 to travel through the body 204. Notably, the body 204 can include features of other embodiment discussed herein.

With particular reference to FIG. 7, an electric-powered heating element 212 is sized and configured to fit within a hollow portion of the body 204 just below the bowl 206 so as to abut the bowl 206 opposite the heating surface 208. The heating element 212 can be configured in many ways. In a preferred embodiment the heating element employs one or more resistive coils embedded in a ceramic or quartz material. The heating element 212 can also have various shapes. For example, in one embodiment the heating element can be substantially flat. In the illustrated embodiment the heating element 212 is generally bowl-shaped so as to fit complementarily about at least part of the bowl 206 and to maximize the heated surface area. In some embodiments, only the portion of the heating element 212 abutting opposite the heating surface 208 is heated. In other embodiments the heating element may direct heat to the heating surface 208 and also side surfaces of the bowl 206. In some embodiments, an insulative heating element cover (not shown) may be employed about an outer surface of the heating element so that heat from the heating element is directed only to the bowl 206, and other parts of the body 204 and surrounding components can be protected from the heat generated by the heating element.

In the illustrated embodiment, a housing cap 214 fits atop the housing 202. It is to be understood, however, that in other embodiments the housing can have a single-piece construction. Further, a removable lid 216 can be configured to fit within the hollow cap 214. When the lid 216 is in place, an enclosed vaporizing chamber is defined between the bowl 206 and lid 216. By enclosing the vaporizing chamber, vaporizing heat can be conserved, leading to more complete vaporization. Also, vapor losses to the atmosphere can be reduced, as the only path for vapor to exit the vaporizing apparatus will be to flow through the passages 210.

With continued reference to FIGS. 6 and 7, electric power can be supplied by a battery assembly 220. In the illustrated embodiment the battery assembly comprises a battery 222, such as a conventional AAA-sized battery, disposed within a battery sleeve 224, which provides electrical connections. A secondary battery sleeve 226 can encompass the battery sleeve 224, and preferably has a decorative role. A battery cap 228 encloses the lower end of the battery assembly 220. A battery crown cap 230 is disposed atop the battery 222. Preferably the crown cap 230 includes a mount portion 232.

A circuit board housing 234 includes a mount portion 236 that is configured to engage the crown cap mount portion 232, such as through a threaded engagement. Preferably, physical engagement of the circuit board housing 234 and crown cap 230 via their respective mount portions 236, 232 also provides an electrical connection so that power from the battery assembly 220 is communicated to the circuit board housing 234. Preferably, the connection between the battery assembly 22o and the circuit board housing 234 is within the housing 202.

As best shown in FIG. 6, when the battery assembly 220 is engaged with the circuit board housing 234, a portion of the battery assembly 220 extends out of the lower portion 203 of the housing 202. The battery assembly 220 is shaped and configured so that there is a space between the outer surface of the battery assembly 220 and the inner surface of the housing lower portion 203 so as to provide a vapor flow path through the lower portion 203.

In the illustrated embodiment, the battery assembly 220 is detachable from the vaporizer 200 so that the user may, for example, replace the AAA battery 222. It is to be understood that, in other embodiments, the battery assembly may include a rechargeable battery. It is also to be understood that battery assemblies can be removed and replaced with other battery assemblies.

In a preferred embodiment, the circuit board housing is attachable to the body 204, such as via a threaded connection. In additional embodiments the circuit board housing can be incorporated into the body. In still further embodiments, the circuit board housing and body may not be in any abutting connection, and the circuit board housing can be separately supported within the housing 202, such as within a portion of the lower part 203 of the housing. Also, in some embodiments the cap 214 threadingly engages the upper end of the housing 202. In some embodiments the cap engages part of the body 204 so as to constrain the body within the housing, and perhaps to securely hold the body sandwiched against an internal shoulder of the housing. In other embodiments the body is separately mounted within the housing, such as by a friction fit, and the cap simply aligns with the body.

Continuing with reference particularly to FIG. 7, a circuit board 240 is configured to fit within the circuit board housing 234, preferably being securely held in place by tracks 238 formed in a wall of the housing 234. The illustrated circuit board 240 includes an actuator button 242 that communicates with electronic control componentry 244. The circuit board 240 is in electric communication with the heating element 212, such as via wires (not shown). The electronic control componentry 244 is configured to control electric power delivery to the heating element 212. In a preferred embodiment, the actuator button includes a lamp (not shown)

A button 250 is connected to an elongate rod 252 having a distal end 254. Preferably aligned holes (not shown) are formed in the housing 202 and circuit board housing 234, which holes accommodate the elongate rod 252 extending therethrough, with the button 250 being accessible from outside the housing 202. As such, when a user pushes the button 250, the distal end 254 of the rod 252 contacts and depresses the actuator button 242, which in turn triggers the electronic control componentry 244 to supply electric power to the heating element 212, which electric power preferably is provided in accordance with a control routine.

In some embodiments in which the actuator button includes a lamp, the button 250 can be configured to communicate light from the actuator button 242 to the outside of the housing 202, such as by the button 250 having a translucent portion that is lit up by the light. Further, in a preferred embodiment, the actuator button lamp is lit when power is being delivered to the heating element 212. Thus, the button light serves as a visual indicator that the heating element 212 is energized, whether or not the button 250 is currently depressed.

In the illustrated embodiment, the electronic componentry 244 controls power delivery in accordance with one of two operational modes, which are herein referred to as a manual mode and an automatic mode. In the manual mode, depressing the button 250 triggers power delivery to the heating element 212, and power is delivered until the button is released. Thus, in manual mode, the user directly controls the length of time the heating element 212 is energized by holding the button 250 in the depressed position.

Preferably the control componentry is configured to not allow the heating element to be energized for too long of a time. For example, in the illustrated embodiment, the control componentry 244 is configured to track and limit the length of time the heating element 212 is continuously energized. More specifically, if the user holds the button 250 down for longer than 10 seconds, the control componentry 244 will trigger the device to reset, thus terminating power delivery to the heating element. Also, in some embodiments the control componentry may be linked to sensors that track the temperature of the heating surface 208, and if the temperature exceeds a trigger value the control componentry will reset the device or, in another embodiment, reduce the current supplied to the heating element 212 so as to correspondingly reduce the temperature.

In the automatic mode, depressing the button 250 signals the control componentry to energize the heating element for a set time period of 10 seconds, regardless of whether the button is held down or not.

The button can be used to change the vaporizer 200 from the automatic mode to the manual mode, and vice versa. In the illustrated embodiment, quickly depressing the button 5 times within a time period of 2 seconds will effect a change from one mode to the other. Also, upon a change in mode, a visual indicator is provided to signal the change in mode and to signal which mode is set. For example, 3 blinks of the lamp indicate that the vaporizer has been set to the manual mode, and 6 blinks of the lamp indicate that it has been set to the automatic mode.

It is to be understood that, in additional embodiments, more (or less) modes may be employed, and differing methods may be employed for switching between modes. Also, in some additional embodiments, supplemental modes may be provided for controlling factors other than time of operation. For example, in another embodiment, a first supplemental mode will operate the heating element 212 at a first temperature, while second and third supplemental modes operate the heating element at successively higher temperatures. This can be in addition to the manual and automatic primary modes discussed above. In order to set supplemental modes, the user can depress the button in accordance with a preset pattern (such as, for example, two quick presses followed by a long press of more than 1 second), at which time the device will enter a programming condition in which the user can switch between supplemental modes by clicking the button. After each click the lamp will blink to indicate the identified supplemental mode (i.e., 1 long blink for the first supplemental mode, 2 or the second, 3 for the third). When the desired supplemental mode is identified, the user can signal a selection (such as by holding the button down for two seconds), and the indicated supplemental mode will be selected. Once set, the supplemental mode can remain selected, even as the user toggles back and forth between the primary modes (here, manual and automatic).

The embodiments of vaporizing apparatus discussed herein provide numerous advantages. For example, embodiments of the present vaporizing apparatus are sized and configured to be used with typical, or "off-the-shelf," water pipes. Further, the user doesn't need to operate a handheld blowtorch in order to produce the heat necessary to vaporize the combustible material. The user simply pushes the ignition button, which is conveniently integrated into the vaporizing apparatus. Further, the heating surface is advantageously recessed within the vaporizing apparatus, thereby reducing the likelihood that a user will inadvertently touch the hot heating surface.

The components of the present embodiments may comprise various materials, including, but not limited to, glass, ceramic, metals, and/or other materials. For example, the housing and/or the body may comprise a metal, such as aluminum or brass. The heating surface may comprise a metal, such as titanium, or ceramic. The spacer and/or the flame chamber may comprise ceramic.

The foregoing materials may be selected for their advantageous properties, such as high heat tolerance, good heat conductivity or, conversely, poor heat conductivity, low porosity, corrosion resistance, durability when subjected to repeated heating and cooling cycles, resistance to cracking, etc. However, none of the listed materials is in any way limiting. Various of the present embodiments may comprise all, some, or none of the listed materials. Further, the present embodiments may comprise one or more materials not explicitly recited herein, including later developed materials.

The embodiments discussed above have disclosed structures with substantial specificity. This has provided a good context for disclosing and discussing inventive subject matter. However, it is to be understood that other embodiments may employ different specific structural shapes and interactions.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A vaporizing apparatus, comprising:
    a housing having an upper end and a lower end, the lower end being vertically lower than the upper end;
    an air opening formed through the housing;
    a heating surface within the housing vertically below the air opening and communicating with the air opening, the heating surface facing upwardly and configured to support a combustible material upon an upper side of the heating surface and transfer heat to the combustible material;
    a heat source configured to apply heat to the heating surface; and
    a vapor path defined within the housing between the heating surface and a lower opening at the lower end of the housing;
    wherein the lower end of the housing is configured to engage an upper end of a water pipe downstem so that the apparatus is supported on the downstem and the lower opening communicates with a lumen of the downstem; and
    wherein the vaporizing apparatus is configured so that the combustible material on the upper side of the heating surface generates a vapor when the heat source is activated to apply heat to the heating surface, and such vapor follows the vapor path downwardly past the heating surface to exit the vaporizing apparatus through the lower opening.

2. A vaporizing apparatus as in claim 1, wherein an upper portion of the housing has an outer diameter greater than an outer diameter of a lower portion of the housing, and the lower portion of the housing has a tapered part that has a tapered outer diameter that decreases moving toward the lower end of the housing.

3. A vaporizing apparatus as in claim 2, wherein a first portion of the tapered part has a diameter less than a downstem inner diameter and a second portion of the tapered part has a diameter greater than or equal to the downstem inner diameter, wherein the tapered part engages an inner surface of the downstem and some of the tapered part extends into the downstem.

4. A vaporizing apparatus as in claim 3 additionally comprising a battery assembly, the battery assembly extending through and out of the lower end of the housing when the battery assembly is engaged and electrically connected to the vaporizing apparatus.

5. A vaporizing apparatus as in claim 1, wherein a body is mounted within the housing and defines a bowl comprising the upper side of the heating surface and a wall that extends vertically upwardly from the heating surface so that the bowl opens upwardly, and wherein the vapor path extends through the body.

6. A vaporizing apparatus as in claim 1, wherein the heat source comprises an electrically-powered heating element.

7. A vaporizing apparatus as in claim 6 additionally comprising a controller and an actuator button, the controller configured to control power delivery to the heating element in connection with a plurality of control modes, each of the control modes controlling the manner in which power is delivered to the heating element while power is being delivered.

8. A vaporizing apparatus as in claim 7, wherein the controller is configured so that a user can select between the plurality of control modes by actuating the actuator button according to a preset pattern.

9. A vaporizing apparatus as in claim 7, wherein the controller is configured to prevent energizing of the heating element beyond an elapsed time.

10. A vaporizing apparatus as in claim 8, wherein in a first mode the controller is configured to energize the heating element for a specified time period when the actuator button is actuated without regard to a time period for which the actuator button is actuated, and wherein in a second mode the controller is configured to energize the heating element only when the actuator button is being held in an actuated position.

11. A vaporizing apparatus as in claim 6 additionally comprising a lid configured to be removably attached to the housing so as to close the air opening and define a vaporizing chamber between the lid and the heating surface when the lid is attached, and wherein the heating surface is accessible via the air opening when the lid is not attached.

12. A vaporizing apparatus as in claim 1, wherein the housing has a longitudinal axis, and the vapor path is radially spaced from the axis.

13. A vaporizing apparatus as in claim 12, additionally comprising an energy source configured to provide energy to power the heat source, wherein the vapor path is spaced radially from the energy source.

14. A vaporizing apparatus as in claim 13, wherein the energy source is aligned with the housing longitudinal axis.

15. A vaporizing apparatus as in claim 6 additionally comprising a battery within the housing, wherein the vapor path passes by the battery.

16. A vaporizing apparatus, comprising:
a housing having an upper end and a lower end, the lower end being vertically lower than the upper end, the housing having a longitudinal axis;
a heating element within the housing;
a medium support within the housing and in contact with the heating element, the medium support configured to support vaporizing medium so that the vaporizing medium is atomized when the heating element is actuated;
an air opening formed through the housing vertically higher than the medium support and in communication with the medium support;
a lower opening formed through the housing lower end;
a vapor path defined within the housing and spaced from the longitudinal axis, the vapor path extending between the medium support and the lower opening at the housing lower end;
a battery assembly in the housing, the vapor path extending past the battery assembly;
the housing lower end being configured to engage an upper end of a water pipe downstem so that the apparatus is supported on the downstem and the lower opening communicates with a lumen of the downstem; and
wherein the vaporizing apparatus is configured so that atomized vaporizing medium is mixed with air from the air opening to form vapor, and the vapor follows the vapor path downwardly to exit the vaporizing apparatus through the lower opening.

17. A vaporizing apparatus as in claim 16, wherein the housing has a longitudinal axis, and the vapor path is radially spaced from the axis.

18. A vaporizing apparatus as in claim 17, wherein the battery assembly is aligned with the longitudinal axis.

19. A vaporizing apparatus as in claim 17, wherein the lower opening is vertically below an upper opening of the downstem when the apparatus is supported on the downstem.

20. A vaporizing apparatus as in claim 16, wherein the medium support is accessible through the air opening, the apparatus configured so that vaporizing medium can be advanced through the air opening and placed on the medium support.

* * * * *